United States Patent [19]

Wilson et al.

[11] 3,935,944
[45] Feb. 3, 1976

[54] DIAGNOSTIC DISPLAY PACKAGE

[75] Inventors: John C. Wilson, Anaheim; Robert Schiff, Mission Viejo, both of Calif.

[73] Assignee: Baxter Laboratories, Inc., Deerfield, Ill.

[22] Filed: June 10, 1974

[21] Appl. No.: 477,563

[52] U.S. Cl. .............. 206/223; 206/45.34; 206/72; 206/232; 260/803; 220/20
[51] Int. Cl.² B65D 1/36; B65D 69/00; B65D 85/00
[58] Field of Search ... 128/2 R, 2 G; 206/45, 45.34, 206/72, 223, 228, 232, 370, 372, 373, 438, 803; 220/8, 20, 82; 211/128, 134; 248/146; 312/114, 117; D83/1 B, 1 U

[56] References Cited
UNITED STATES PATENTS

| | | | |
|---|---|---|---|
| 2,822,916 | 2/1958 | Wark et al. | 206/228 |
| 3,206,012 | 9/1965 | Braginetz | 206/228 |
| 3,272,319 | 9/1966 | Brewer | 206/370 X |
| 3,300,055 | 1/1967 | Rohr | 211/128 X |
| 3,442,378 | 5/1969 | Wolfe | 206/72 |
| 3,695,452 | 10/1972 | Surman | 206/45.34 UX |
| D120,125 | 4/1940 | Korda | 206/45.34 UX |

Primary Examiner—William Price
Assistant Examiner—Steven E. Lipman
Attorney, Agent, or Firm—Lawrence W. Flynn; Louis Altman

[57] ABSTRACT

There is disclosed a package comprising a rack and a surrounding cover therefor. The rack has a top surface which slopes downwardly from front to rear. This top surface has a plurality of recesses or wells into which small receptacles may be inserted and thereby supported in the rack. The said receptacles are sufficiently large so that they visibly protrude from the rack. As a result of this protrusion of the receptacles the cover has a hood-like configuration to make allowance therefor. The rack also has a rearwardly positioned slot means to receive and support a diagnostic plate and a forwardly positioned trough to hold a tube member.

7 Claims, 8 Drawing Figures

3,935,944

DIAGNOSTIC DISPLAY PACKAGE

BACKGROUND OF THE INVENTION

A considerable number of new diagnostic tests have been developed recently for use in the clinical laboratory. These tests frequently require a number of pre-mixed reagents, applicators and diagnostic plates or slides. With the plethora of such tests, the number of pre-mixed reagents has also multiplied. Unfortunately, such reagent bottles for one test can become confused with the reagent bottles of one or more other tests. Heightening the difficulties is the fact that the reagent bottles are quite diminutive as it is frequently necessary to employ very small quantities of both to-be-analyzed sample and reagent. Moreover, if any of the components required for the diagnostic test are not readily at hand, delay in conducting the test will be caused. Consequently, a rack arrangement adapted for multiple uses to retain and visibly exhibit all of the means required for a specific test would indeed be useful.

SUMMARY OF THE INVENTION

The present invention is designed to ingeniously solve the aforementioned considerable problems. This is achieved by a rack arrangement having a downwardly sloping top surface from rear to front. This surface has positioned therein a number of wells or recesses. One of such recesses is an elongated trough across essentially the front facing portion of the top surface. This trough accommodates an elongated horizontally-disposed receptacle. Rearwardly and upwardly thereof is a plurality of additional recesses. The walls and bottom thereof have a cage-like configuration. Also, for wide adaptability, those wells not needed for a specific diagnostic test are covered with removable plates. A cover is also provided to enclose the entire rack except for the bottom. The cover is retained by suitable detent means and preferably is constructed of a transparent plastic material to permit visibility of the rack contents. Also the rack has a slot means rearward of the top surface to retain a diagnostic plate in upstanding position. In this manner, all of the necessary component parts of the reagent bottle, tube, applicator, and diagnostic plate, are kept in a convenient and visible manner and utilize a minimum of space.

DETAILED DESCRIPTION OF THE INVENTION

Figure 1:
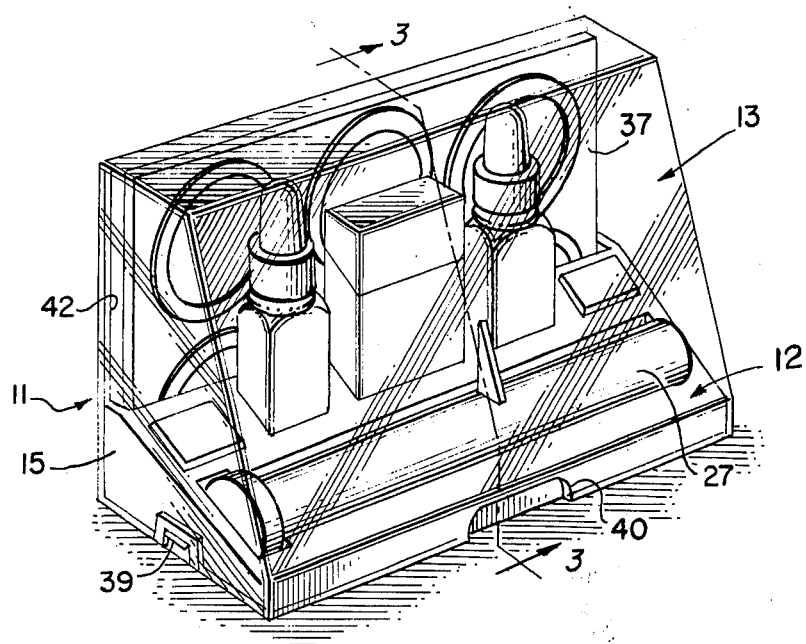
FIG. 1 is a perspective view of the display package of the present invention.

Now, turning to the drawings for a detailed consideration of the invention, attention is directed to FIG. 1 from which the display package 11 of the present invention may be viewed. It will be readily seen that the display package 11 includes a rack 12 and a cover 13 therefor, the latter preferably being constructed of transparent plastic, for example, clear polystyrene.

The cover 13 comprises a back wall 14, two end walls, namely, a left-end wall 15 and a right-end wall 16. The cover also has a roof 17 and downwardly outwardly sloping therefrom between the said end walls a mansard front wall 18 terminating in a downwardly extending skirt 19. The cover, then, describes a complete housing, except that it is not supplied with a bottom. The bottom is seen to be supplied by the presence of the rack 12.

The rack 12 has a right-end wall 20 and a left-end wall 21. It has a sloping forwardly facing surface 22 terminating in a front wall 23. The surface 22 possesses a number of wells 24 each of which is adapted and constructed to retain a receptacle which may contain useful ingredients for performing a plurality of tests.

Figure 2:
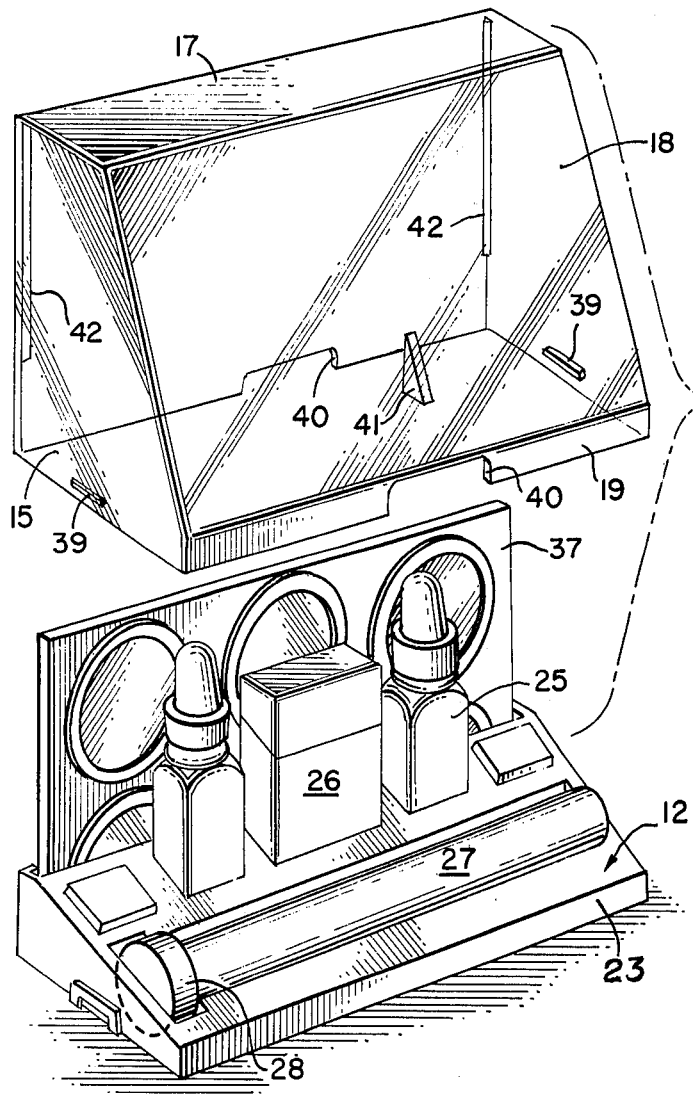
FIG. 2 is a similar view as in FIG. 1 wherein the cover has been exploded therefrom.
Figure 4:
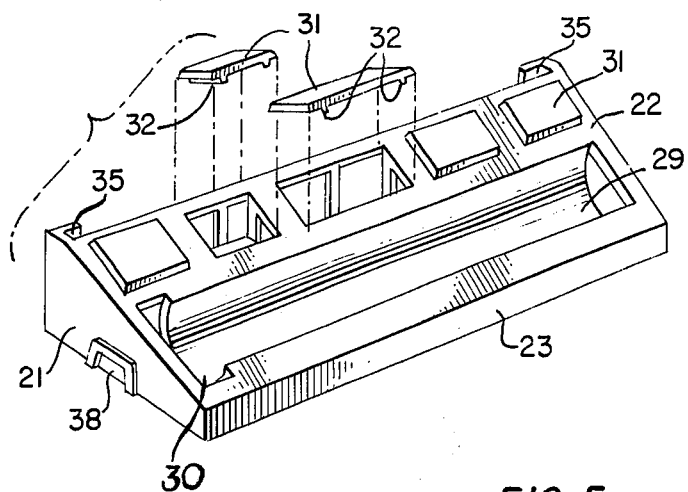
FIG. 4 is a perspective view of the rack portion of the display package of the present invention with knock-outs being exploded therefrom.

FIGS. 1 and 2 depict the fact that the rack 12 is provided with a row of wells 24 having rectangular openings and another well which is an elongated trough 29 positioned downwardly and forwardly therefrom. A plurality of wells 24 are square and contain square bottles having eye dropper caps therein. The square well and bottle shape constitutes holding means for opening and closing the reagent bottles without removal from the display package. One of wells 24 is rectangular and contains a small rectangular carton 26. This carton is adapted for holding a plurality of applicator sticks and can have a perforated opening for convenient dispensing. Elongated trough 29 is adapted for holding elongated tube 27 having a cap 28. Turning to FIG. 4, it will be noted therefrom that elongated well 29 is provided with a rounded bottom for seating of the tube 27 and slot 30 to accommodate the cap 28 of the tube 27. As the rack 12 is hollow, the slot 30 is nonsupporting for the cap 28, but this does not constitute a problem as adequate support is found in the remainder of the wall 29.

Figure 6:
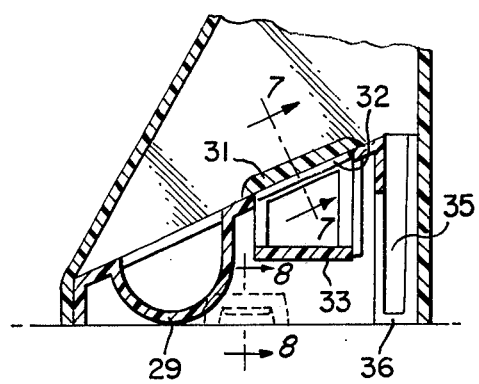
FIG. 6 is a cross-sectional view taken along line 6—6 of FIG. 5.
Figure 7:
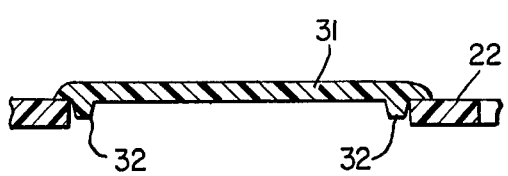
FIG. 7 is a fragmentary cross-sectional view taken along line 7—7 of FIG. 6.

In back of well 29 are a plurality of rectangularly-shaped wells penetrating through the surface 22. Knock-out plates 31 cover these wells as shown in FIG. 4 where two plates 31 are exploded therefrom. FIGS. 6 and 7 give a more succinct view of the knock-out plates 31 which have friction-engaging ribs 32 whereby they are retained in the openings of the wells.

Figure 5:
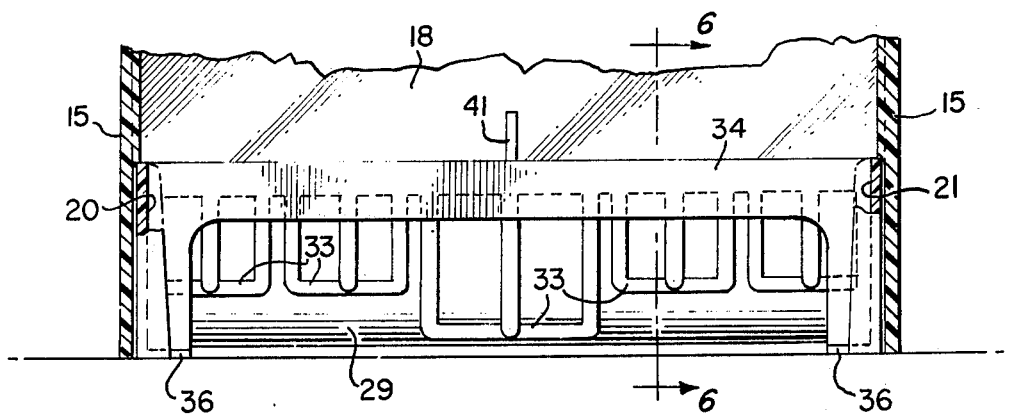
FIG. 5 is a cross-sectional view taken along line 5—5 of FIG. 3.

The wells are constructed as a cage 33 having downwardly extending ribs to form the sides of the cage and normal thereto cross ribs to form the bottom thereof. The cages do not extend to the bottom of rack 12 but this is essentially merely a matter of choice. The openings provided by the cages 33 make it possible to forcibly dislodge the knock-out plates from the bottom thereof by an instrument poked through the cages. This may be accomplished through the back wall 34, as seen in FIG. 5, which describes an inverted U-shaped configuration.

Figure 3:
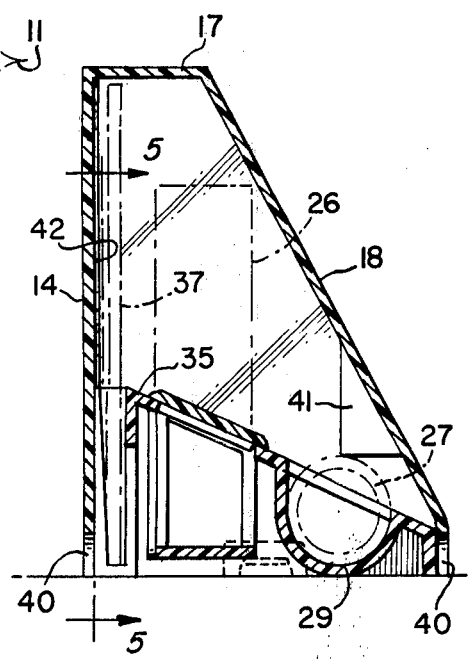
FIG. 3 is a cross-sectional view taken along line 3—3 of FIG. 1.

Each of the end walls 20 and 21 have rearwardly extending portions constituting oppositely disposed vertical slots 35, each having a bottom 36. These slots are adapted and constructed to carry a diagnostic plate 37 as depicted in FIGS. 1 and 2 and shown by dotted lines in FIG. 3.

Figure 8:
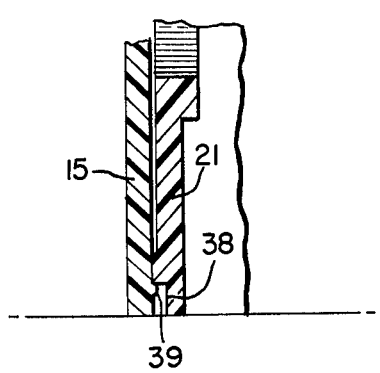
FIG. 8 is a fragmentary cross-sectional view taken along line 8—8 of FIG. 6.

The cover 13 has a number of interesting features not heretofore discussed. For instance, it will be appreciated that the cover fits quite snugly about the rack 12. FIGS. 1, 3, 5 and 6 demonstrate this quite clearly. To further insure a good fit with a cover-retaining feature, a detent 38 is provided at the left and right-end walls of the rack 12. These detents accept small projection 39 as shown in detail in FIG. 8.

To provide ease in lifting or removing the cover 13, the back wall 14 and skirt 19 each possess a finger notch 40 whereby the rack 12 with its cover may be held in the palm of one hand. Finger notch 40 can be enlarged to accommodate several fingers. The rack is restrained from movement by grasping it through the just-mentioned notches while with the other hand the cover is removed, defeating the detent-holding means.

Internally of the front wall 18 of the cover is a triangularly-shaped rib 41. This rib performs the useful function of assisting in retaining in place the tube 27, as more elucidated in FIG. 1.

Another ingenious feature to be found in the cover 13 are the corner ribs 42 located in the corner of the cover where the left and right-end walls of the cover come together with the back wall 14 of the cover. The corner ribs 42 extend from the top of the cover to a point above the slot-carrying portion of the rack 12. The corner ribs act as rearward abutment means to prevent the cover 13 from being put on too far. Front abutment is determined by the height of front wall 23 of the rack 13 and the skirt 19 of the cover 13.

The display package of the present invention can be readily constructed of thermosetting resins, each portion, namely, the rack and cover can be integrally molded by suitable injection molding techniques. The knock-out plates can also be integrally molded, but they can be separately fabricated and assembled to cover the wells. By making the cover transparent as herein illustrated, the display package is not only attractive but permits ready identification of the ingredients of the package.

Representative of a complete diagnostic test which can be stored in the display package of this invention is a diagnostic test for infectious mononucleosis. Such tests and the reagents therefor are described, for example, in U.S. Pat. Nos. 3,426,123 and 3,708,572. In the present example, three glass reagent bottles 25 with dropper caps and one paperboard carton 26 containing 60 wooden applicator sticks are provided in a row of wells 24 in the rearward upper part of surface 22 of rack 12. One of these reagent bottles contains 2.5 ml. of a fixed horse erythrocyte suspension; a second reagent bottle contains 1.0 ml. of positive control serum which is a reactive human serum containing 0.1 percent sodium azide as a preservative; and the third reagent bottle contains 1.0 ml. of negative control serum which is normal human serum also containing 0.1 percent sodium azide as a preservative. The fifth well 24 in this row will be capped with plate 31 as being not required for this test. Alternatively, the rack 12 can be molded with only four, instead of five, wells in this row. A capped tube 27 containing 50 capillary pipettes, 0.053 inch I.D. × 3.940 inches length, is provided in an elongated trough 29 positioned in the lower, forward part of surface 22 of rack 12. A clear glass slide 37, 4¾ inches × 3⅛ inches × 1 1/16 inches diameter, is positioned upright in vertical slots 35*. The rack 12 is covered with a rigid, transparent polystyrene cover 13. All of the components of the diagnostic test are thereby compactly contained in the display package. They are clearly visible to the laboratory technologist upon opening the refrigerator in which the display package is desirably stored for maintaining activity of the reagents. Sufficient test materials are supplied for sixty tests and the technologist can at any time readily ascertain the approximate number of tests remaining

*The symbol " represents inches, by rapid observation of the display package.

The diagnostic test in this example is carried out as follows:

1. The reagents are allowed to reach room temperature (20°–25° C).
2. A capillary pipette is used to deliver one drop of the patient's serum into the center of a well on the glass slide.
3. One drop each of the positive control serum and the negative control serum are placed into the center of separate wells on the same test slide.
4. One drop of the fixed horse erythrocyle suspension (thoroughly mixed) is added to each of the test wells.
5. The contents of each test well are mixed thoroughly with a separate applicator stick and each mixture is spread within the entire well area.
6. The slide is rotated from side to side by hand for two minutes and examined for macroscopic agglutination against a black background using indirect light.
7. The test specimen results are compared to the control serum results. Negative results are indicated by a smooth or finely granular suspension as shown by the negative control serum. Positive results are indicated by a strong macroscopic agglutination as shown by the positive control serum.

All of the test materials for the foregoing diagnostic test are thus built into a permanent polystyrene console that is a unified, functional working center. Everything required for the diagnostic test stays together whether in use or in storage. The technologist need never remove the reagent or controls from the display package. Set-up and storage are greatly simplified. The problems of spillage and misplaced components are virtually eliminated. The tough, clear console cover and the positioning of the components in the rack keeps everything clean, compact and visible.

It will be appreciated that the display package of the present invention is not limited to the components required in the foregoing diagnostic test but also is adaptable to other diagnostic tests, for example, diagnostic tests for HCG (human chorionic gonadotropin) and various latex diagnostic tests as described in U.S. Pat. No. 3,088,875 which require the use of glass slides, capillary pipettes, mixing means and a variety of reagents, depending upon the specific test.

Various other examples will be apparent to the person skilled in the art after reading the foregoing specification without departing from the spirit and scope of the invention. All such further examples are included within the scope of the appended claims.

What is claimed is:

1. A display package comprising a rack, said rack having a front wall, two end walls, and a top wall, said top wall sloping downwardly from rear to front, said top wall having a plurality of wells, each of said wells adapted and constructed to carry at least a portion of a receptacle, one of said wells being an elongated trough means positioned downwardly and forwardly of the other said wells, said end wells of said rack extending rearwardly and each having therein a slot in oppositely disposed relationship adapted and constructed to carry a plate upright therebetween, a cover, said cover having a top wall, back wall and end walls, said cover having a front wall sloping downwardly from rear to front terminating in a skirt means overlying the front wall of said rack, the dimensions of said cover being such as to essentially surround said rack.

2. The display package of claim 1 wherein at least one of the said wells has foraminous walls and a bottom.

3. The display package of claim 2 wherein at least one of said wells has a removable cover means.

4. The display package of claim 3 wherein said cover is retained on said rack by a detent means.

5. The display package of claim 4 wherein the sloping front wall of said cover has internally secured thereto rib means adapted and constructed to retain a receptacle in at least one of the said wells.

6. The display package of claim 5 wherein the said cover has abutment means internally thereof adapted and constructed to abut against said rack.

7. The display package of claim 1 wherein a plurality of wells are rectangular and adapted to hold rectangular shaped receptacles.

* * * * *